United States Patent [19]

Greene et al.

[11] Patent Number: 4,913,164

[45] Date of Patent: Apr. 3, 1990

[54] EXTENSIBLE PASSIVE FIXATION MECHANISM FOR LEAD ASSEMBLY OF AN IMPLANTABLE CARDIAC STIMULATOR

[75] Inventors: Donald R. Greene, Phoenix, Ariz.; James I. Bradshaw, Surfside, Tex.

[73] Assignee: Intermedics, Inc., Angleton, Tex.

[21] Appl. No.: 249,977

[22] Filed: Sep. 27, 1988

[51] Int. Cl.[4] ............................................. A61N 1/05
[52] U.S. Cl. ................................. 128/785; 128/419 P
[58] Field of Search .................... 128/785, 419 P, 783, 128/784, 786, 639, 642; 604/105, 106

[56] References Cited

U.S. PATENT DOCUMENTS

| | | | |
|---|---|---|---|
| 2,854,983 | 10/1958 | Baskin | 604/105 |
| 3,397,699 | 5/1966 | Kohl | 128/785 |
| 3,902,501 | 9/1975 | Citron et al. | 128/785 |
| 4,033,357 | 7/1977 | Helland et al. | 128/419 P |
| 4,043,338 | 8/1977 | Homm et al. | 604/105 |
| 4,378,023 | 3/1983 | Trabucco | 128/785 |
| 4,407,303 | 10/1983 | Akerström | 128/785 |
| 4,419,819 | 12/1983 | Dickhudt et al. | 128/785 |
| 4,506,679 | 3/1985 | Mann | 128/785 |
| 4,519,404 | 5/1985 | Fleischhacker | 128/785 |
| 4,549,557 | 10/1985 | Hakki | 128/785 |
| 4,564,023 | 1/1986 | Hess | 128/785 |
| 4,590,949 | 5/1986 | Pohndorf | 128/785 |

FOREIGN PATENT DOCUMENTS 3300050   7/1984   Fed. Rep. of Germany ...... 128/785

OTHER PUBLICATIONS

Porstmann et al., "P-Wave Synchronous Pacing," 7-1972, pp. 74-76, American Journal of Cardiology.

Primary Examiner—Lee S. Cohen
Assistant Examiner—Kennedy J. Schaetzle
Attorney, Agent, or Firm—John R. Merkling

[57] ABSTRACT

An implantable lead for a cardiac stimulator has an electrode at its distal end, and resilient, non-penetrating, tissue-contacting elements integral with the lead in the vicinity of the electrode. The resilient elements are movable from a first unextended position for ease of insertion or withdrawal of the lead through the vein of a patient to a second extended position for contacting tissue to retain the electrode in a selected location in the heart of the patient. A device operable along the lead serves to selectively move the resilient elements from the unextended to the extended position or vice versa.

20 Claims, 2 Drawing Sheets

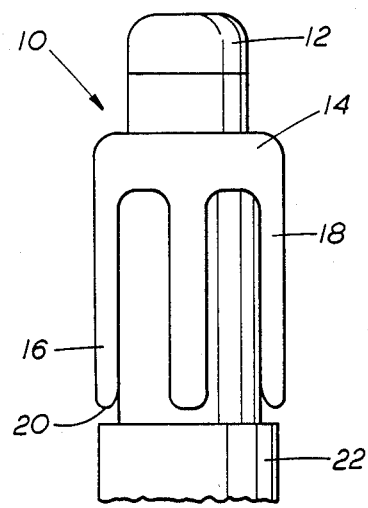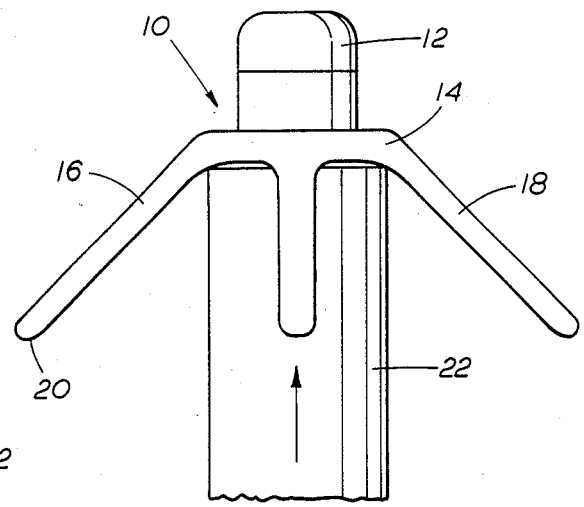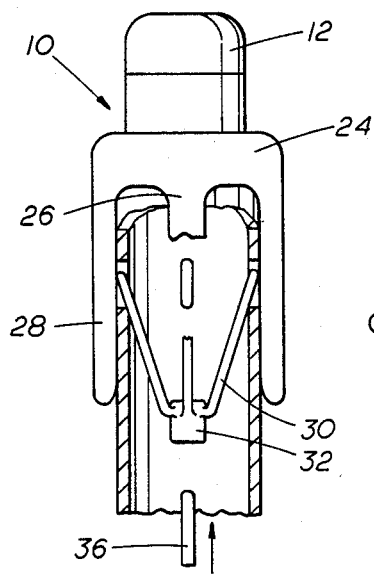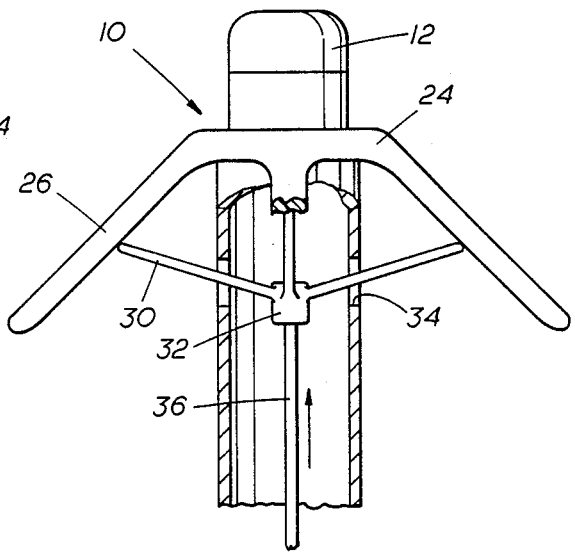

EXTENSIBLE PASSIVE FIXATION MECHANISM FOR LEAD ASSEMBLY OF AN IMPLANTABLE CARDIAC STIMULATOR

BACKGROUND OF THE INVENTION

1. Field of the Invention

The present invention relates generally to implantable cardiac stimulators, such as artificial pacemakers, cardioverters and defibrillators; and more particularly to fixation mechanisms for the lead/electrode assemblies of implantable cardiac stimulators.

2. Discussion of Prior Art

The sinoatrial (S-A) node of the human heart acts as the natural pacemaker by which rhythmic electrical excitation is developed and propagated to the atria, whereupon the atrial chambers contract, pumping blood into the ventricles. The rhythmic excitation is further propagated through the atrioventricular (A-V) node, which imposes a delay, and then via the conduction system consisting of the bundle of His and the Purkinge fibers to the ventricular myocardium, producing contraction of the ventricles. As a result, the oxygen-depleted blood in the right ventricle is pumped through the pulmonary artery to the lungs, and the oxygenated blood in the left ventricle is pumped through the arteries to the body. The right atrium receives the oxygen-depleted blood from the body via the veins, and the left atrium receives oxygenated blood from the lungs.

The actions repeat in a rhythmic cardiac cycle in which the atrial and ventricular chambers alternately contract and pump, relax and fill. One way valves along the veins, between the chambers in the right side and the left side of the heart, and at the exits of the right ventricle and left ventricle prevent backflow of the blood as it moves through the heart and circulatory system.

The S-A node is spontaneously rhythmic, and with a normal excitation and propagation system the heart beats in an organized manner at a regular rate termed sinus rhythm. Disruption of the natural pacing and propagation system as a result of aging or disease is commonly treated by artificial cardiac pacing, in which a cardiac pacemaker is implanted to maintain the desired heart rate.

Implantable artificial cardiac pacemakers, or, more simply, "pacemakers," generally employ a stimulus generator commonly termed a "pulse generator" housed in a case and powered by a self-contained battery, and a lead assembly typically referred to simply as a "lead" having one or more electrodes for conductive coupling to the generator circuitry via a connector integral with the case. The pacing electrode is variously referred to as the stimulating cathodic electrode, the stimulating electrode, or merely the cathode, and the indifferent electrode is alternatively referred to as the reference electrode, the anodic electrode, or simply the anode. The pulse generator and the lead are manufactured and distributed as separate items, the leads being interchangeable with pulse generators of the various types.

Typically, the lead is inserted through the superior vena cava (the great vein which transports unoxygenated blood from the upper part of the body to the right atrium) until the stimulating electrode at the distal end of the lead is brought into proper position within the desired chamber in the right side of the patient's heart. Because it is adapted for intravenous insertion, the lead is sometimes referred to as a "catheter lead"; and because the electrode is adapted to be positioned within the heart, it is often called an "endocardial electrode". The proximal end of the lead is inserted and fastened into the integral connector of the pulse generator case, which is implanted in a subcutaneous pouch formed by an incision in the patient's chest. With dual chamber pacemakers, both chambers of the heart may be stimulated and/or sensed using two separate leads, one of which is introduced into the right atrium and the other into the right ventricle.

By appropriately manipulating the lead, the implanting physician positions and, if necessary, repositions the stimulating electrode to assure consistent "capture" of the heart, that is to say, that the patient's heart responds to each stimulus generated by the pacemaker. In essence, the stimulating electrode serves to impress an electric field, resulting from electrical discharge by the pulse generator, on excitable myocardial tissue in the vicinity of that electrode. This is accomplished via an electrical circuit consisting of the pulse generator, the conducting lead, the stimulating electrode, the indifferent electrode, and the volume conductor comprising the patient's body tissue and fluid.

The pacemaker may be arranged for unipolar or bipolar stimulation according to the configuration and location of the indifferent electrode. For unipolar stimulation, the anode is somewhat remote from the heart, typically constituting part of the metal case that houses the pulse generator. For bipolar pacing, the lead to be implanted is configured with the cathode and the anode insulatively separated from but in close proximity to one another at the distal end of the lead. Typically the cathode is located at or near the tip of the lead and the anode is configured as a ring electrode spaced back one half inch or so from the cathode. Each electrode is connected to its own electrically conductive coil within the lead.

The stimulating electric field generated by the pacemaker in the vicinity of the cathode must be of sufficient impulse strength to initiate a so-called "action potential" and depolarization of cells within the excitable tissue, in order to cause and propagate cardiac stimulation. The smallest electrical impulse necessary to initiate such stimulation is referred to as the "stimulation threshold," or simply the "threshold". In practice, the cardiologist or surgeon will set the stimulation level to comfortably exceed the threshold for the particular patient and pacing system. Indeed, since there is invariably an acute but gradual rise in threshold over a period of from about one to four weeks after the pacemaker is implanted, it is customary to set the stimulus level initially at about four times that of the threshold measured at implant. The increase in acute threshold is attributable in part to the growth of a fibrotic layer of non-excitable tissue of uneven thickness about the electrode tip in contact with the myocardium, which effectively increases the surface area of the electrode and lowers the current density. Another factor is the inflammation reaction at the tip. The chronic threshold is usually observed about four to eight weeks after implantation.

It is common practice to seek to position the stimulating cathodic electrode at the time of implant at a location within the chamber to be paced which offers the lowest threshold and the greatest mechanical stability. Until the stimulating electrode becomes secured in place as a result of fibrotic growth, a period which depends in large measure on the structure and composition of the electrode, it is subject to dislodgement because of the rhythmic contraction and relaxation of the heart, or merely as a consequence of general body movements of the patient.

Various electrode fixation mechanisms have been devised since the inception of the artificial pacemaker to secure the lead (and more particularly, the electrode) in place after positioning by the cardiologist or surgeon. Such mechanisms fall into two categories. Some offer passive fixation, by means of non-invasive devices such as pliant barbs (so-called "tines") attached at or near the lead tip to engage the trabeculae within the heart chamber. Others provide more positive fixation termed "active fixation," of the electrode. The known active fixation mechanisms include corkscrews, hooks, piercing barbs, or other anchoring means arranged at or near the lead tip for penetration of the endocardium upon manipulation of the lead and/or a stylet traversing the lead, following proper positioning of the cathode.

The principal disadvantages of active fixation mechanisms are that (1) they are quite difficult to manufacture, and are therefore very costly, because of the relatively small size of the lead and the necessarily tiny size of the functioning parts of the mechanism which must be attached to the distal end of the lead; (2) they require penetration of the tissue which can cause trauma, particularly if the lead must be unhooked for repositioning of the electrode and re-affixed to the tissue at a more desirable location for lower threshold capture, or if the lead must be withdrawn; and (3) they can make the lead extremely difficult to implant unless the surgeon is highly accomplished in the techniques of inserting, positioning, manipulating and affixing a lead with that particular mechanism by having performed the procedure numerous times. With respect to the latter disadvantage, it is recognized that implanting surgeons tend to develop a "feel" for leads having particular fixation mechanisms, and express a certain comfort level with their own favorites, sometimes to the point of being unable to achieve a successful implant with leads having other types of fixation, despite a high level of skill.

That partiality also extends to leads having various types of passive fixation. The latter mechanisms also suffer disadvantages, including the fact that leads utilizing them typically are not easily threaded through the vein, and the mechanism tends to be dislodged from the tissue or not be easily seated in place during implantation, as may be expected when one is dealing, by definition, with less positive fixation. Nevertheless, leads with passive fixation devices are much easier to reposition during implantation than are leads with active fixation devices once having engaged and penetrated the tissue. Furthermore, the passive fixation-type leads are typically less complex and therefore easier to manufacture than the active fixation leads.

It is a principal object of the present invention to provide a new and improved passive fixation mechanism for cardiac stimulating or sensing electrodes.

A serious problem with previous approaches to passive fixation of the lead/electrode is that the anchoring means is permanently deployed to contact tissue for seating once the stimulating electrode is positioned to achieve capture. Accordingly, the lead is not easily threaded through the vein. Moreover, some of the tined-types of leads tend to become so enmeshed in the trabeculae that re-positioning of the lead/electrode approaches the order of difficulty encountered with some of the active fixation leads. In this respect, it should be noted that the threshold for a seated lead/electrode may be considerably higher than had been observed just prior to the seating, requiring that the electrode be re-positioned.

Accordingly, it is another object of the present invention to provide an improved passive fixation mechanism for a catheter lead which allows the lead to be inserted easily through the vein for placement of the electrode in proper position in the desired heart chamber, and which further enables the lead to be withdrawn readily or the electrode to be disengaged and repositioned easily to a different location to provide a lower threshold for capture.

SUMMARY OF THE INVENTION

Briefly, according to the present invention an implantable lead for a cardiac stimulator has an electrode at its distal end, and is provided with resilient, nonpenetrating, tissue-contacting elements integral with the lead in the vicinity of the electrode. The resilient elements are movable from a first unextended position for ease of insertion or withdrawal of the lead through the vein of a patient to a second extended position for contacting tissue to retain the electrode in a selected location in the heart of the patient. A device operable along the lead serves to selectively move the resilient elements from the unextended to the extended position or vice versa.

According to a presently preferred embodiment of the invention, the passive fixation mechanism for a pacemaker lead includes spaced, pliant, non-penetrating, tissue-engaging fingers or tines fastened at one end to the distal end of the lead in the vicinity of the stimulating (and/or sensing) electrode, the fingers being movable from a normal retracted position against the surface of the lead to an extended position at an angle to the lead for engagement of tissue. A collar or sleeve slidable longitudinally along the surface of the lead is utilized to selectively force the fingers to the extended position after the lead has been inserted through the patient's vein and it is determined that the electrode is properly located relative to excitable myocardial tissue in the selected chamber of the heart for low threshold capture. In this manner, the fingers are positioned to engage the trabeculae and thereby retain the electrode in the selected location. The fingers are sufficiently resilient to return to the normal retracted position when not influenced by the slidable collar, i.e., when the collar is withdrawn back beyond the tips of the fingers.

Preferably, the fingers are integral with, i.e., extend from a second collar which is secured to the lead surface in the vicinity of the electrode, with the free ends of the fingers pointing away from the electrode.

In an alternative preferred embodiment of the invention, the fingers are moved from one position to the other by means of a hub or plunger movable axially internally of the lead. A plurality of spaced substantially radially projecting members are coupled to the hub for movement therewith. These projecting members, when moved, exert forces on or withdraw forces from the fingers to move the fingers from the normal retracted position to the extended position and back to the normal retracted position when the hub is moved axially toward and away from the electrode, respectively.

In one configuration of this alternative embodiment, the plurality of projecting members comprise spaced struts each coupled at one end to the hub for pivotal movement therewith. The struts are movable through an angular sector relative to the axis of the lead via holes in the lead wall, and each of the struts is pivotally connected at its other end to a respective one of the fingers, whereby to move the fingers from the normal retracted position to the extended position and back to the normal retracted position with movement of the hub axially toward and away from the electrode, respectively.

In another configuration of this alternative embodiment, the projecting members, when moved axially with the hub, produce a moving deformation of a flexible sheath on the wall of the lead, which, in turn, urges the flexible fingers outwardly from the lead body when the hub is moved toward the electrode, and allows the fingers to return to their normal unextended position when the hub is moved away from the electrode.

Thus, yet another object of the invention is to provide an implantable lead for a cardiac stimulator, in which the lead is provided with tissue-contacting means that are selectively movable from a first position to a second position, or vice versa, where one of the first and second positions allows easy insertion of the lead through the patient's vein to position the stimulating electrode for low threshold capture of excitable myocardial tissue in the selected chamber, and the other of the first and second positions extends the tissue-contacting means into engaging relationship with other tissue in the chamber to retain the electrode in the selected location.

BRIEF DESCRIPTION OF THE DRAWINGS

The foregoing and still further objects, features and attendant advantages of the present invention will become apparent from a consideration of the following detailed description of a presently preferred embodiment and alternative embodiments, taken in conjunction with the accompanying drawings in which:

FIGS. 1 and 2 are side views of the distal end of a lead/electrode assembly incorporating one presently preferred embodiment of the passive fixation mechanism according to the present invention;

FIGS. 3 and 4 are partly sectional side views of the distal end of a lead/electrode assembly incorporating another embodiment of a passive fixation mechanism according to the invention.

DETAILED DESCRIPTION OF THE PREFERRED EMBODIMENTS

Figure 5:
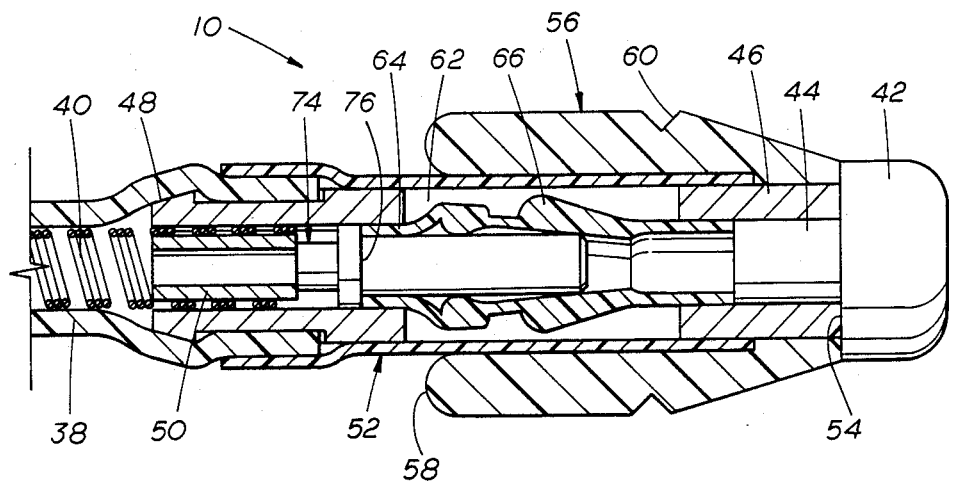
FIGS. 5 and 6 are partly sectional side views of the distal end of a lead/electrode assembly incorporating still another alternative embodiment of a passive fixation mechanism according to the invention.

Referring now to FIGS. 1 and 2, a currently preferred embodiment of a passive fixation mechanism according to the present invention is provided in conjunction with the electrode assembly at the distal end of a lead 10 for use with a cardiac pacemaker. Except as otherwise expressly described herein, lead 10 is of conventional construction. The type of lead shown in all of the Figures is configured for unipolar stimulation of the heart, but the structure and operation of the passive fixation mechanisms of the preferred and alternative embodiments to be described are usable irrespective of whether the mode of stimulation is unipolar or bipolar. Furthermore, it will be understood that although the embodiments of the invention specified herein are described in the context of a cardiac pacemaker, the invention may be employed in any environment in which a lead or electrode is to be secured to tissue accessible via the vascular system.

At its distal end, the lead 10 includes a stimulating cathodic electrode 12 disposed at the lead tip. Cathode 12 may be fabricated of any material conventionally employed for cardiac stimulating electrodes, such as titanium or platinum-iridium alloy, but is preferably composed of a titanium substrate coated on its exposed surface with a thin layer of iridium oxide, in the manner described in U.S. Pat. No. 4,679,572 of Ross G. Baker, Jr., assigned to the same assignee a is the present invention. The cathode is electrically connected in the usual manner to a conductive coil (not shown) which extends the entire length of lead 10 and terminates in a male connector (not shown) for mating with a female connector integral with the case that houses the pulse generator.

The wall of lead 10 is composed of a conventional biocompatible inert material such as polyurethane. In the preferred embodiment, a collar 14 composed of similarly biocompatible material such as polyurethane or silicone rubber has a plurality of fingers or tines 16 projecting therefrom. Collar 14 is constructed to slide onto and fit snugly over the surface of the lead. To assure its retention, the collar 14 is secured to the outer surface at the distal end of the lead in the vicinity of the electrode 12 by use of a conventional biocompatible medical grade adhesive, such as Dow Medical Adhesive Silicone Type A. The fingers or tines 16 projecting from the collar, however, are free to be moved outwardly of the lead. In practice, the fingers are formed integral with the collar 14 by cutting material from an original tube whose length corresponds to the desired length of the fingers plus the width of the remaining collar.

The collar 14 is assembled onto the lead such that the fingers 16 are pointing away from the electrode 12. The tip 18 of each finger 16 is cut slightly to provide a lip which is spaced slightly from the surface of lead 10, as indicated at 20, for reasons which will become apparent presently. The cut surfaces are preferably smoothed to assure that no surface is present that is likely to penetrate tissue. The composition of the collar-finger structure is sufficiently rigid to assure that the fingers 16 will normally remain seated against the surface of the lead wall as shown in FIG. 1, i.e., when no contrary forces are imposed or present on the lead. However, the fingers are also sufficiently resilient to be lifted from the lead wall under forces exerted outwardly on them, and to return to their normal flattened or retracted position against the outer surface of the lead when released, in the absence of other constraints. In other words, the material of which the fingers and collar are composed has a "memory," so that when the material is temporarily deformed and released, it will return to its original form within a relatively short period of time absent other restraints or constraints. In this normal retracted position, the fingers lie alongside the surface of the lead and will not impede the movement of the lead when it is implanted by the surgeon by threading the lead through the vein of the patient and into the heart.

A second sliding collar or telescoping outer sheath 22 composed of polyurethane is disposed on the lead to slidably engage the tips 18 of the fingers 16, as the sheath 22 is advanced toward the electrode tip 12. In particular, the sheath 22 initially engages the tips 18 of fingers 16 at the notched-back lips 20 so that further advance of the sheath serves to spread the fingers 16 outwardly from the lead 10 to extended positions at an angle to the lead surface, as shown in FIG. 2. In the partly or fully extended position, the fingers 16 are suitably arranged to engage the trabeculae but are sufficiently pliant to preclude their penetration of tissue so that the lead may be retained with the electrode 12 in proper position at a location of relatively low threshold capture as determined by the physician with the lead connected to the pulse generator of the pacemaker. If it is desired to change the location of the electrode, the outer sheath 22 is pulled back, and the lead 10 is advanced slightly to free the fingers 16 and allow them to return to the retracted position. In this manner, the physician has the capability to manipulate the lead at will, and to re-seat the lead any number of times without difficulty, or to withdraw the lead entirely, unlike the difficulties encountered with conventional tined leads. The telescoping sheath 22 preferably runs virtually the entire length of the lead for that purpose. Alternatively, if a shorter sliding collar is used, it may be coupled to an axially movable hub which is displaced by means of a stylet inserted into the lead, in a manner similar to another embodiment shown in FIGS. 3 and 4.

Referring now to FIGS. 3 and 4, an alternative embodiment of an implantable lead having a passive fixation mechanism in the form of an extensible-retractable tissue-contacting means generally includes a combination of collar 24 and fingers 26 substantially similar to that described above for the embodiment of FIGS. 1 and 2. The combination of collar and fingers or tines is also fastened to the lead body in the same manner as in the aforementioned preferred embodiment. Here, however, each of the fingers 26 is pivotally connected, at a suitable point between its tip 28 and the point of coupling to the collar 24, to a respective strut 30 which itself is pivotally connected to a central hub 32 axially movable within the interior of lead 10. Small slots 34 in the lead wall allow the struts to project therethrough without binding when the hub undergoes axial translation within the limits of its movement.

In practice, the hub and the struts are molded in a single piece construction, preferably of Delrin or Celcon. To provide the pivotal coupling between the struts and the hub, the struts are necked down (in the molding process) at those points. In this way, the hub 32 can move freely within a limited range along the axis of the lead in the direction toward the electrode 12, under the force exerted by a stylet 36 manipulated by the implanting physician, without binding of the struts at the edges of the respective holes in the lead wall. The struts 30 are secured to the respective fingers at their opposite ends by use of medical adhesive of the type described earlier. When the advancing force of the stylet is removed from the hub, the resiliency of the finger-collar combination and the pivotal connections of the struts with the fingers and the hub allow the fingers to return to the normal retracted position. Thus, when it is being implanted in the patient, the lead may be introduced through the vein with the fingers in that normal flattened position. Upon placement of the stimulating electrode in position to achieve capture in the desired chamber at the right side of the heart, stylet 36 is pushed against hub 32 to spread the fingers to the extended position suitable for engaging tissue to seat the lead and retain the electrode in that position. When the stylet is then withdrawn, the fingers remain engaged within the trabeculae. If it is desired to reposition the lead at the time of implant, the lead need only be advanced slightly to allow the fingers to disengage from the trabeculae and return to the normal retracted position.

For purposes of ease of construction, the lead wall is separated at the lines of the holes so that the hub-strut single molded piece may be inserted into the lead body. The struts are then adhesively fastened to the fingers and the two sections of the lead are adhesively secured with the aforementioned Dow Medical Adhesive or any other suitable biocompatible sealant.

Figure 6:
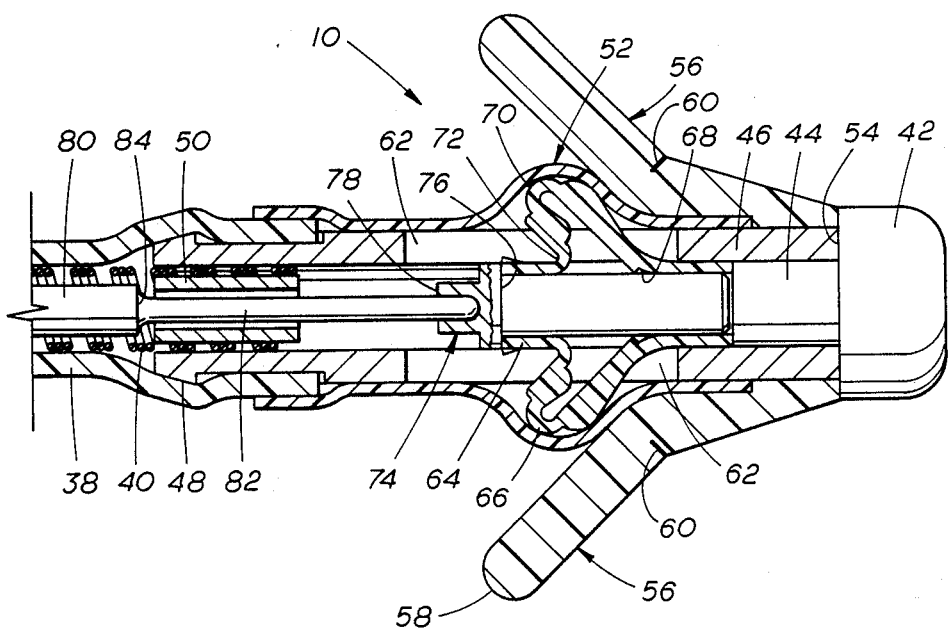

With reference now to FIGS. 5 and 6, another alternative embodiment of the invention provides the implantable lead 10 with a passive fixation mechanism in which the tissue-contacting means is, like the other embodiments, normally in the flat position. As before, the tubular wall 38 of the lead is composed of a suitable conventional biologically inert material, preferably polyurethane, which provides an elongate housing for a conductive coil 40 electrically connecting the cathodic tip electrode 42 to a desired point of the circuit contained within the pulse generator housing (not shown) at the proximal end of the lead. Of course, additional electrically conductive coils may be carried within the lead depending on the number of electrodes and functions performed.

According to the embodiment of FIGS. 5 and 6, a centrally disposed shaft 44 integral with the electrode tip 42 is maintained in electrical contact with a stainless steel tube 46 by virtue of an interference fit between the shaft and the tube. At the opposite end 48 of tube 46, the electrical coil 40 is maintained in electrical contact with and mechanically secured to a portion of the interior surface of the tube 46 by a press fit of the coil between the tube 46 and a smaller diameter and shorter length stainless steel tube 50. Thereby, the coil 40 is electrically connected to the electrode tip 42, and the entire mechanism is securely fastened together.

The distal end of the lead wall 38 and the conductive tube 46 extending therefrom is surrounded by a flexible sheath 52 composed of any conventional biocompatible inert material, preferably silicone rubber, which abuts against the underside surface or shoulder 54 of electrode tip 42. At the outer surface of the sheath 52, a plurality of longitudinally extending fingers or tines 56, preferably equally spaced circumferentially about the distal end of the lead and composed of any appropriate flexible biocompatible material, such as silicone rubber, are adhesively attached to the sheath along a portion of their lengths nearest the tip shoulder 54. Here again, the attachment may be achieved by means of Dow Medical Adhesive of the aforementioned type. In this manner of attachment, the tines 56 extend away from the shoulder 54 and normally lie flat against sheath 52. The tines are pliant, but sufficiently rigid to maintain their shape, and have rounded tips 58 to preclude injury to the vascular wall or trauma to cardiac tissue with which they will come into contact when the lead is deployed for use during original implantation of the pacemaker or replacement of the lead. Preferably, three or four tines 56 are utilized on the lead, for stability of the lead after implantation.

Each of the tines is notched at, for example, one-third to one-half of its length measured from the electrode tip shoulder 54. By way of example, the notch 60 extends about halfway through the diameter of the respective tine, and is located at the tine surface away from the sheath 52 to allow the tine to flex upon exertion of a force outwardly from the lead at the tip of the tine. To that end, the adhesion of each tine to the sheath is preferably only from the point of the underside of shoulder 54 to or slightly beyond the point at which the notch 60 is located.

Depending upon the number of tines utilized in the lead embodiment of FIGS. 5 and 6, the conductive tube 46 is provided with a corresponding number of, and similarly circumferentially spaced, longitudinal slots 62 (FIG. 6). A cylindrical expansion member 64, preferably composed of Delrin, is configured to be received in tube 46 and has a plurality of thin ears 66 formed longitudinally along its surface aligned with the respective equally numbered slots 62 of the tube 46. The ears 66 are profiled to have areas of flexibility 68, 70, 72 in order to extend from the slots 62 when member 64 is longitudinally collapsed. The projection of the ears 66 from the slots 62 is sufficient to cause flexible sheath 52 to be deformed to the shape of the ears at the locations of any interference between the two. Because interference is intended to occur, according to this embodiment of the invention, the surface of each ear is rounded or smoothed at the points of such interference. A plunger 74 has a first portion axially received in the member 64, shoulder 76 bearing against an end of member 64, and an oppositely directed cup 78.

A special stylet 80 (FIG. 6) is provided in combination with the lead 10 to extend therethrough and to engage the plunger 74, for purposes of deploying the tines 56 when the lead has been implanted with the electrode tip 42 properly positioned within the desired chamber at the right side of the patient's heart. To that end, the stylet has a first diameter of 0.014-0.016 inch, for example, over its entire length except for a tip portion 82 of substantially equal desired length of travel to the plunger 74, where the stylet has a smaller diameter of, say, 0.010 inch with a shoulder 84 between the two portions of different diameter.

The smaller diameter portion 82 of the stylet 80 is adapted to be received within the central bore of sleeve 50 and into cup 78 of plunger 74. The shoulder 84 abuts the sleeve 50 to stop the stylet travel thus limiting the force applied to plunger 74. Movement of the stylet inwardly of the lead 10 forces the plunger 74 to collapse member 64 forcing ears 66 to form outwardly. As the ears 66 expand into interference with the sheath 52, the latter is deformed at those points. With further movement of the stylet into the cavity, the points of deformation increasingly exert radial forces against the respective tines 56 at corresponding points of contact therewith. In response, the tines are urged to flex at the point of each notch 60, thereby causing the tips of the tines to be deployed outwardly from the position flat against the lead wall to a position at an acute angle with the lead wall, as shown in FIG. 6.

It would be possible to arrange this embodiment so that as the stylet is withdrawn, the tines seek to return to their normal position flat against the wall by memory of the material. Alternatively, it would be possible to have external threads on stylet tip 82 engage in internal threads in cup 78 to draw the plunger back thereby pulling the member to restore it to its original condition.

In the course of implanting the lead, the implanting physician will leave the stylet in its withdrawn position, so that the tines lie flat against the wall of the lead to permit the lead to be readily inserted through the vein and into the desired chamber of the heart. When the stimulating electrode is properly positioned in the chamber, the physician will then introduce the stylet into position to deploy the tines outwardly, so that a slight tug on the lead engages them in the trabeculae. When the electrode is properly seated in place and capture is occurring, the stylet is withdrawn.

Although certain presently preferred embodiments of the invention have been described herein, it will be apparent to those persons skilled in the field to which the invention pertains that variations and modifications of the described embodiments may be implemented without departing from the true spirit and scope of the invention. For example, the invention need not be limited to us with pacemakers (or related medical devices, such as defibrillators), but may be employed with any device intended to electrically stimulate a part of the body through the vascular system. Accordingly, it is intended that the invention be limited only to the extent required by the appended claims and the applicable rules of law.

What is claimed is:

1. A passive fixation mechanism for an endocardial lead with a distal and a proximal end and a stimulating electrode on said distal end comprising:

a plurality of flexible tine means each adapted to be fastened at one end to the distal end of the lead in the vicinity of the electrode for engaging tissue without penetration thereof, each of said tine means resiliently biased to lie in a position parallel to a distal surface of said lead with a respective free end thereof pointing away from the electrode but being sufficiently flexible to be moved outwardly to a position at an angle to and projecting from the distal surface of said lead from the respective fastened end thereof, and deploying means for selectively forcing each of the tine means outwardly to said angled position for engaging tissue at the respective free end thereof.

2. The invention of claim 1, wherein said deploying means moves said plurality of tine means in unison to said projecting position.

3. The invention of claim 1, wherein said deploying means is a sliding sleeve adapted to slide on the surface of said lead.

4. The invention of claim 1, wherein said deploying means includes a plurality of spaced member means coupled to an axially movable hub means internally of said lead, each of said member means being moved with the hub means into and out of force exerting relationship with a respective one of said tine means such that when the hub means is moved axially toward and away from the electrode the plurality of tine means is moved respectively to the projecting position and the parallel position.

5. The invention of claim 4, wherein each of said members comprises a strut extending through the surface of said lead and pivotally connected to a respective one of said tine means.

6. The invention of claim 1, wherein said deploying means includes hub means for axial movement internally of said lead, said hub means comprising a plurality of spaced projection means for exposing said line means, such that when the hub means is moved axially toward and away from the electrode the plurality of tine means is moved respectively to the projecting position and the parallel position.

7. The invention of claim 1, further including a collar adapted to be secured to the surface of said lead in the vicinity of the electrode, and wherein the fastened end of each of the tine means is integral with said collar.

8. The invention of claim 1, wherein each of said tine means comprises elastomeric means for returning said tine means to said parallel position when said deploying means is reversed.

9. Apparatus for use with a pacemaker, comprising:
a lead having a proximal and distal end;
an electrode carried on the distal end of said lead;
spaced, pliant, non-penetrating, tissue-engaging fingers fastened at one end to said lead in the vicinity of said electrode, said fingers being resiliently biased in a retracted position against the lead and movable from said retracted position to an extended position at an angle to the lead for engagement of tissue, and
means coupled to said lead for selectively moving said fingers from said retracted position to said extended position.

10. The invention according to claim 9, wherein said moving means moves said fingers in unison to said extended position.

11. The invention according to claim 9, wherein said moving means comprises a sliding sleeve on the surface of said lead.

12. The invention according to claim 9, wherein said moving means includes a hub means for axial movement internally of said lead, a plurality of spaced member means each projecting radially from said hub means and movable therewith for moving said fingers from the retracted position to the extended position and back to the retracted position when the hub means is moved axially toward and away from the electrode, respectively.

13. The invention according to claim 12, wherein said members comprise struts each coupled at one end to said hub means for pivotal movement therewith, a plurality of holes in a distal surface of said lead accommodating respective ones of said struts for movement therethrough, each of said struts pivotally connected at the other end thereof to a respective one of said fingers.

14. The invention according to claim 9, further including a collar secured to a distal surface of said lead in the vicinity of the electrode, and wherein the fastened end of each of the fingers is integral with said collar.

15. The invention according to claim 9, wherein each of said fingers returns to said retracted position when said moving means is reversed.

16. An apparatus for use with cardiac stimulators, comprising an implantable lead having a distal and a proximal end; an electrode at a distal end of said lead; means for electrically connecting said electrode to a proximal end of said lead; resilient, non-penetrating, tissue-contacting means integral with said lead in the vicinity of said electrode and movable from a first unextended position for ease of insertion of the lead through the vein of a patient to a second extended position for contacting tissue to retain the electrode in a selected location in the heart of the patient, and vice versa, said tissue-contacting means being resiliently biased to lie in said first unextended position when unrestrained other than as being an integral part of the lead; and means operable along the lead for selectively moving said tissue-contacting means from one of said first and second position to the other.

17. The invention of claim 16, wherein said moving means comprised a sliding sleeve on said lead.

18. The invention of claim 16, wherein said moving means includes hub means for limited axial translation internally of said lead, and urging means projecting from said hub means and movable therewith for forcing said tine means from the unextended position to the extended position in response to selective translation of the hub means toward the electrode under the influence of said moving means.

19. An electrical lead with a passive fixation mechanism, the lead having an electrode at a distal end thereof for stimulating tissue of the body after implantation of the lead via the vascular system, said passive fixation mechanism further comprising
spaced, pliant, non-penetrating, tissue-engaging tine means projecting from said lead in the vicinity of and in a direction away from said electrode, resiliently biased to a substantially flattened position against the lead and movable from said substantially flattened position against the lead to a deployed position at an acute angle to the lead, for selective engagement of tissue, and
means adapted to be coupled to said lead for selectively moving said tine means from the substantially flattened position to the deployed position.

20. The invention of claim 19, wherein said moving means is reversible to return said tine means from the deployed position to the substantially flattened position.

* * * * *